(12) United States Patent
Travish et al.

(10) Patent No.: US 11,177,105 B2
(45) Date of Patent: Nov. 16, 2021

(54) X-RAY SOURCE

(71) Applicant: Adaptix Ltd., Begbroke (GB)

(72) Inventors: Gil Travish, Oxford (GB); Paul Betteridge, Witney (GB); Mark Evans, North Leigh (GB); Martin Holden, Wantage (GB); Abdul Sami Mughal, Oxford (GB); Kristen Schmiedehausen, Los Altos, CA (US)

(73) Assignee: Adaptix Ltd., Begbroke (GB)

( * ) Notice: Subject to any disclaimer, the term of this patent is extended or adjusted under 35 U.S.C. 154(b) by 81 days.

(21) Appl. No.: 16/389,692

(22) Filed: Apr. 19, 2019

(65) Prior Publication Data

US 2019/0252148 A1 Aug. 15, 2019

Related U.S. Application Data

(63) Continuation of application No. PCT/GB2016/053259, filed on Oct. 19, 2016.

(51) Int. Cl.
| | |
|---|---|
| *H01J 35/30* | (2006.01) |
| *H01J 35/06* | (2006.01) |
| *A61B 6/02* | (2006.01) |
| *A61B 6/14* | (2006.01) |
| *A61B 6/00* | (2006.01) |
| *H01J 35/14* | (2006.01) |

(52) U.S. Cl.
CPC .......... *H01J 35/065* (2013.01); *A61B 6/025* (2013.01); *A61B 6/14* (2013.01); *A61B 6/4007* (2013.01); *A61B 6/56* (2013.01); *A61B 6/587* (2013.01); *H01J 35/14* (2013.01); *H01J 2235/068* (2013.01)

(58) Field of Classification Search
CPC .......... H01J 35/06; H02J 35/14; A61B 6/025; A61B 6/4007; A61B 6/4233; A61B 6/5205; A61B 6/4488; A61B 6/482; A61B 6/102
See application file for complete search history.

(56) References Cited

U.S. PATENT DOCUMENTS

| | | | |
|---|---|---|---|
| 5,598,454 | A | 1/1997 | Franetzki et al. |
| 7,218,700 | B2 | 5/2007 | Huber et al. |
| 7,496,178 | B2 | 2/2009 | Turner |
| 7,664,222 | B2 | 2/2010 | Jabri et al. |
| 10,217,598 | B2 | 2/2019 | Evans et al. |
| 10,524,743 | B2 | 1/2020 | Travish et al. |
| 2004/0240616 | A1 | 12/2004 | Qiu et al. |
| 2008/0240343 | A1 | 10/2008 | Jabri et al. |

(Continued)

FOREIGN PATENT DOCUMENTS

| | | |
|---|---|---|
| EP | 1463085 | 9/2004 |
| GB | 2523796 | 9/2015 |

(Continued)

OTHER PUBLICATIONS

Brazilian Patent and Trademark Office, "Search Report," dated Jul. 2020.

(Continued)

*Primary Examiner* — Don K Wong
(74) *Attorney, Agent, or Firm* — Ryan Alley IP

(57) ABSTRACT

A portable x-ray imaging source (100) capable of motion-free x-ray tomosynthesis, wherein said source is suitable for dental and small body-part/small area imaging.

20 Claims, 3 Drawing Sheets

(56) References Cited

U.S. PATENT DOCUMENTS

| | | |
|---|---|---|
| 2010/0172475 A1 | 7/2010 | Behling |
| 2011/0075802 A1 | 3/2011 | Beckmann et al. |
| 2011/0122992 A1 | 5/2011 | Hanke et al. |
| 2011/0188634 A1 | 8/2011 | Lee et al. |
| 2012/0051510 A1 | 3/2012 | Yasunori et al. |
| 2014/0010349 A1 | 1/2014 | De Godzinsky et al. |
| 2015/0124934 A1 | 5/2015 | Gupta et al. |
| 2017/0162359 A1* | 6/2017 | Tang ............... H01J 35/065 |
| 2019/0029611 A1* | 1/2019 | Travish ............ A61B 6/107 |

FOREIGN PATENT DOCUMENTS

| | | |
|---|---|---|
| JP | 3022259 | 3/1996 |
| JP | 2007-522894 | 8/2007 |
| JP | 2008-253762 | 10/2008 |
| JP | 2012-066060 | 4/2012 |
| JP | 2013-154254 | 8/2013 |
| JP | 2014508619 | 4/2014 |
| JP | 2014184346 | 10/2014 |
| JP | 2017-533010 | 11/2017 |
| WO | 2008/155715 | 12/2008 |
| WO | 2011017645 | 2/2011 |
| WO | 2015132595 | 9/2015 |

OTHER PUBLICATIONS

EPO, Examining Division Communication, dated Jan. 30, 2020.
WIPO, International Search Report and Written Opinion in corresponding PCT application PCT/GB2016/053259, dated Jul. 17, 2017.
Zhang et al., "Stationary scanning x-ray source based on carbon nanotube field emitters", Applied Physics Letters, Apr. 29, 2005.
JPO, Translation of Search Report in corresponding JP application 2019-517925, dated Aug. 24, 2020.
JPO, Translation of Notice of Reasons in corresponding JP application 2019-517925, dated Aug. 28, 2020.
IP India, Examination Report in IN Application 201947016438, dated Feb. 18, 2021.
JPO, Machine Translation of Reasons for Refusal in JP Patent Application 2019-517925, dated Feb. 25, 2021.
CNIPA, "Search Report," dated Nov. 25, 2020.

* cited by examiner

X-RAY SOURCE

RELATED APPLICATIONS

This application claims priority under 35 U.S.C. § 120 to, and is a continuation of, co-pending International Application PCT/GB2016/053259, filed Oct. 19, 2016 and designating the US. This International application is incorporated by reference herein in its entirety.

FIELD

The present invention generally relates to an x-ray imaging source, and more particularly, to a portable x-ray imaging source capable of motion-free, tomosynthesis imaging, and suitable for dental and small body-part/small area imaging.

BACKGROUND

Conventional x-ray imaging is commonly based on planar radiography. This approach utilizes a single, high-power point-like x-ray source made up of a set of vacuum-tubes capable of generating a single cone or fan beam of x-rays over a wide range of energies and currents.

Such systems typically require the x-ray source be placed a significant distance from the person to be imaged to ensure the x-ray covers a sufficient area, and to maintain a "skin safe distance"—the minimum distance necessary to avoid an excessive x-ray dose at a particular entry point on the skin. This large stand-off distance, or distance between the source and object, necessitates a lot of power. To provide this power, conventional x-ray systems use large, expensive, and heavy (in the tens of kilograms), power supplies. Such power supplies often require cooling, which further adds to the bulk, weight, and cost of the system. The end result is that such conventional systems are typically fixed (not portable) or otherwise occupy a large space, and impose a high capital cost on end users, such as hospitals, primary care facilities, screening clinics, and dental offices.

In addition, such conventional, single-source systems (absent a gantry or other means of moving the source) are generally only capable of generating two-dimensional (2D) images. Conventional two-dimensional (or planar) imaging is often inadequate for identifying features (or biomarkers) essential for clinical detection and diagnostics. This is particularly true in dental and small-body part/small-area imaging, such as mammography.

In dental diagnostics, intraoral (taken inside the mouth) x-rays or radiographs are the most common images used to diagnose dental problems. But because intraoral radiographs are two-dimensional, they often prove to be inadequate for identifying a wide host of clinical issues, including vertical root fractures, bone loss, implant instability; and dental caries (tooth decay)—the latter of which is the most prevalent chronic disease in both children and adults, despite being largely preventable. One particular challenge to dentists is confirming a nerve canal's position relative to the root prior to molar extraction. Currently the best devices for such a procedure are Cone Beam Computed Tomography (CBCT) systems. But due to the high radiation exposure inherent to CBCT, typically 30-150× that of planar dental imaging, the use of CBCT is generally avoided, especially in cases where the danger posed by the condition is not significant enough to merit such exposure. Also, due to the cost of CBCT equipment many dentists do not have access to such systems. Therefore, dentists are frequently required to proceed 'on risk' with limited information from two-dimensional, planar x-ray images as guidance.

Similar issues arise in other small-area imaging applications. For example, mammography is a specialized medical imaging technique that uses x-rays to see inside the breasts, and is an essential medical diagnostic tool in the early detection of breast diseases. But two-dimensional mammography is generally less efficacious than digital breast tomosynthesis, or three-dimensional (3D) mammography. In digital breast tomosynthesis multiple images of the breast, at different angles, are captured and reconstructed or "synthesized" in a three-dimensional image set. Currently breast tomosynthesis requires moving the x-ray source in an arc and stopping at multiple points, thus adding to the cost and total imaging time during which the breast is held in a compressing clamp, leading to patient discomfort.

Population studies show that screening with breast tomosynthesis results in improved early detection of breast cancers, including small cancers that may be difficult to detect with two-dimensional imaging. Breast tomosynthesis also results in fewer "call-backs" or instances of follow-up screenings, greater accuracy in pinpointing the size, shape, and location of abnormalities, fewer biopsies, greater likelihood of detecting multiple tumors, and clearer images of abnormalities.

Radiation dose reduction is also a significant concern in three-dimensional, x-ray imaging. This concern is particularly pressing in the case of Computer Tomography (CT), perhaps the most developed three-dimensional imaging technique available. CT involves moving a source about a subject to collect large numbers of projections (effectively scanning all angles of a patient), and then constructing the data into a usable, three-dimensional image set. This 360 degree scan, leads to patients being exposed to significantly higher x-ray doses than in conventional, planar radiology (circa 1.5 mSv for Low Dose CT (LDCT) and up to 8.0 mSv for full dose CT).

Estimates for 2007 approximate that 29,000 future cancers in the U.S. may be related to CT scans performed in just that year. This high incidence of cancer likely stems from the high x-ray exposure attributable to CT. Indeed, in the United Kingdom in 2008 it was estimated that CT scans made up 68% of the x-ray dose to patients, despite making up less than 10% of all x-ray procedures. Accordingly, a need exists for reducing the number of CT studies across the population, particularly in cases involving pediatrics, multiple screenings or follow-up studies, and patients suffering from chronic disease.

SUMMARY

Digital tomosynthesis provides a viable, lower-dose alternative to CT. Because digital tomosynthesis involves only a partial-angle (or limited sweep) scan of a patient (as opposed to a 360 degree scan), current digital tomosynthesis systems may produce effective radiation doses of less than 1/10th that of low-dose chest CT scans with only a 30% dose increase as compared to conventional, two-view chest radiography (Planar: 0.1 mSv, DT: 0.13 mSv).

Digital tomosynthesis using conventional, single-source based systems is nonetheless limited by the cost and complexity of such systems. Conventional approaches to tomosynthesis typically involve taking multiple images of a stationary object or person from a variety of directions (usually at partial angle of an area of interest on a patient), and then using these multiple, two-dimensional images to reconstruct a three-dimensional image set. Usually, a mechanical gantry is needed to move the single x-ray source (vacuum tubes) along a sequence of locations, which adds to the size and expense of the x-ray system. Also, because the images are taken sequentially, this setup requires a longer overall image capture time than would otherwise be desirable. Because of its cost and complexity, digital tomosynthesis is not generally used in dental applications or, with the exception of mammography and chest imaging, in small area/small body part applications.

Therefore, while conventional two-dimensional (planar) imaging is inadequate for identifying various clinically relevant markers in dental and small-limb/small area applications, CT is often avoided in such cases due to the potential exposure to high-dose radiation. Thus, there is a need to achieve the dose-to-information improvements demonstrated by DT in chest and mammography, but without the costs and complexity inherent to conventional DT systems.

Accordingly, there is a need in the art for a more widely available x-ray source (e.g., portable, less expensive and with a smaller footprint) capable of providing safer (e.g., lower dose), more accurate (three-dimensional) primary diagnostic imaging. To date, there is no portable, motion-free tomosynthesis x-ray system available on the market.

It is an aim of embodiments of the present disclosure to provide a portable x-ray source (at least an order of magnitude smaller than conventional systems), which enables tomosynthesis from a motion-free source. It is a further aim of embodiments of the present disclosure to enable high-resolution, three-dimensional x-ray imaging with only a minimal increase in radiation dose as compared to conventional two-dimensional x-ray imaging.

By way of example, and not limitation, embodiments of the present disclosure may include a portable x-ray source made up of a plurality of x-ray generators. The plurality of x-ray generators may be arranged in a distributed array, wherein each x-ray generator may be individually addressable (or controllable). In this way, the portable x-ray source may be capable of performing partial-angle scanning of a region of interest (as required for tomosynthesis), while requiring shorter stand-off distances, and hence significantly less power.

In addition, the x-ray source may also include a high-voltage power source capable of powering the x-ray generators. In one aspect, the high-voltage power source may be capable of converting battery voltage to high voltage, thus enabling portable applications. The portable x-ray source may further include a mechanism, such as a gross collimator, capable of collimating emitted x-rays to be within a limited area at a given distance between the generators and the object or person to be imaged. The use of a gross collimator in conjunction with smaller stand-off distances reduces the potential for harmful radiation exposure to patients and the source operators.

The distributed x-ray generator array may include a plurality of electron field emitters arranged in an emitter array. In addition, the distributed x-ray generator array may include a plurality of targets made of a material effective at high-energy bremsstrahlung, or otherwise having an area made of such material. The targets may be arranged in an array having a similar configuration to the emitter array, or may be otherwise arranged in pairs, so as to enable electrons emitted from an electron emitter to strike the bremsstrahlung target, and thus produce x-rays. The pluralities of electron emitters and targets may be maintained in a vacuum by, among other things, housing the emitters and targets in a vacuum chamber.

The distributed x-ray generator array may also include a spacer, which may be capable of maintaining a suitable separation between, and insulating, the emitters from the targets. Moreover, the distributed x-ray generator array may include a plurality of emission controllers, such as, but not limited to, selectively powered solenoid coils, capable of controlling the emission of x-rays from each target. The distributed x-ray generator may further include a filter that may serve to block or remove low-energy x-rays, not beneficial to x-ray imaging, and a collimator array, which may serve to narrow the angle of x-rays emitted from the source.

The above and other characteristics, features and advantages of embodiments of the present invention(s) will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DETAILED DESCRIPTION

Figure 1:
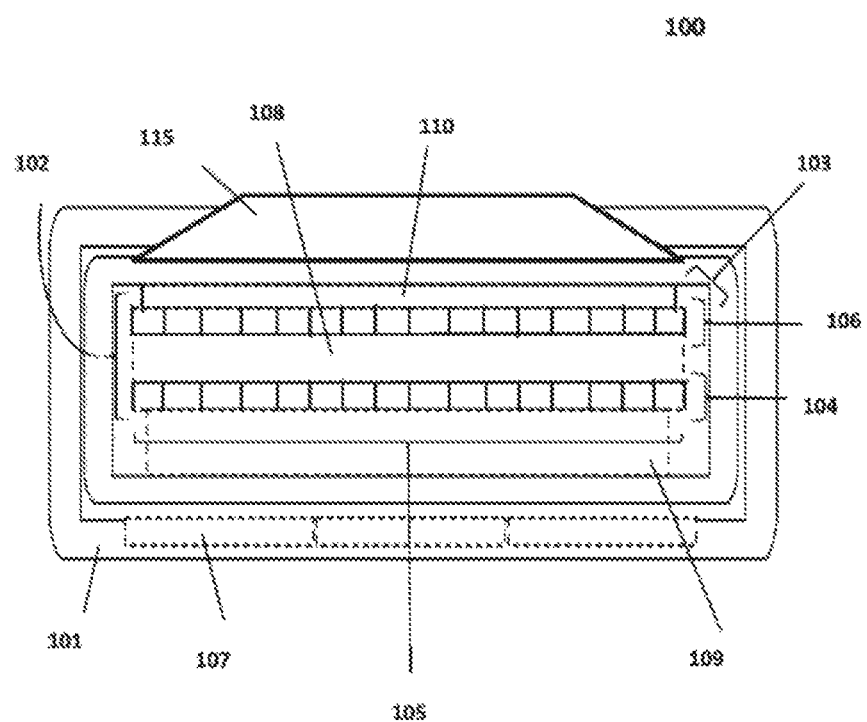
FIG. 1 is an example of an x-ray source in accordance with aspects of the present disclosure.

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any embodiment or aspect of the invention may be combined in any suitable manner, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances.

The principles of the invention will now be described by a detailed description of at least one drawing relating to exemplary features of the invention. It is clear that other arrangements can be configured according to the knowledge of persons skilled in the art without departing from the underlying concept or technical teaching of the invention, the invention being limited only by the terms of the appended claims.

Embodiments of the present disclosure will be described with respect to certain drawings but the invention(s) are not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

FIG. 1 shows an example of a portable x-ray source 100 according to aspects of the present disclosure. Portable x-ray source 100 may comprise a plurality of x-ray generators 102, wherein each x-ray generator 102 may be capable of producing a small cone (or "conelet") of x-ray radiation. The plurality of x-ray generators 102 may be arranged as a distributed x-ray generator array 103, and in one preferred aspect of the present disclosure may comprise a flat-panel, x-ray source (FPS) as described by PCT/US2016/014782 to Travish, et al.

Figure 2:
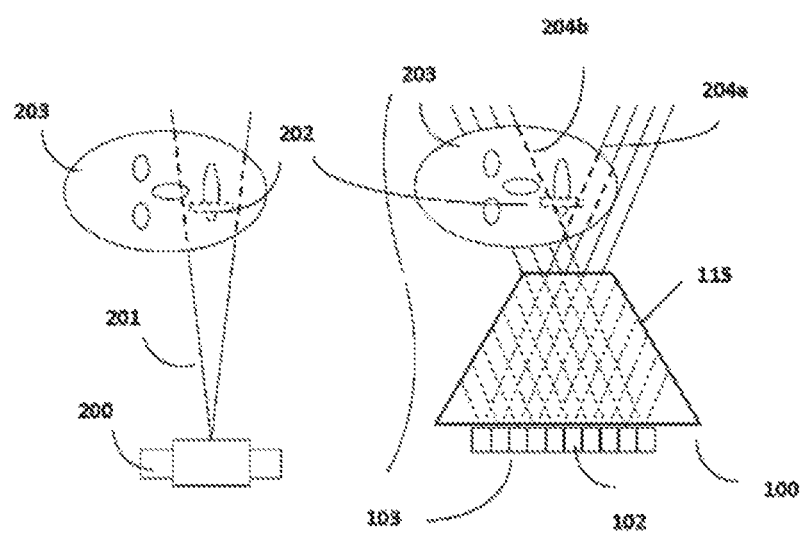
FIG. 2 shows a side-by-side comparison of a conventional single-source, tube-based x-ray source and an example of an x-ray source in accordance with aspects of the present disclosure.

The use of distributed x-ray generator array 103 provides several improvements over current systems, and departs from conventional approaches to x-ray imaging, which generally focus on a single, tube-based (vacuum tube) source and teach away from systems utilizing distributed sources. FIG. 2 provides a side-by-side comparison of a conventional single-source, tube-based x-ray source 200 (as is typically used in dental imaging) to a portable, x-ray source 100 in accordance with aspects of the present disclosure. Tube-based x-ray source 200 is capable of generating an x-ray cone 201. X-ray cone 201 may impinge object 203 (e.g., the patient's mouth), wherein detector 202 may measure the intensity (and hence the attenuation of x-ray cone 201 caused by object 203) to form a two-dimensional radiograph (or shadowgram). For a standard intraoral x-ray scan source 200 must typically be placed at least 20 cm away from object 203.

Conversely, portable x-ray source 100 may include a distributed x-ray generator array 103 (e.g., a fixed, two-dimensional array) comprising a moderate pitch spacing (e.g., in the mm to cm range). Each generator 102 may be individually addressable so as to enable distributed x-ray generator array 103 to produce multiple, angularly-diverse conelets (e.g., conelets 204*a* and conelets 204*b*), which enables portable x-ray source 100 to image object 203 (or more specifically a region of interest) from sufficient angles to generate a three-dimensional reconstruction without need for source movement; in other words, by motion-free tomosynthesis. Because portable x-ray source 100, unlike conventional tomographic systems such as CBCT, does not require expensive precision computer-controlled movers the cost and complexity of portable x-ray source 100 is significantly reduced as compared to conventional systems.

The design of distributed x-ray generator 103 also enables portable x-ray source 100 to be placed closer to detector 202, approximately 12 cm away from object 203 as opposed to the 20 cm in standard intraoral radiography. This reduction in stand-off distance (source to object distance) enables the weight and power requirement of portable x-ray source 100 to be significantly reduced as compared to conventional sources, such as tube-based x-ray source 200. This in turn eliminates the need for costly power supplies, which significantly reduces the cost of portable x-ray source 100 as compared to conventional systems.

The reduction in weight and input power is partially attributable to the fact that radiation declines as a square of distance, as such embodiments of the present disclosure may only require approximately ¼ x-ray intensity (and hence ¼ input power) of conventional systems. The design of distributed x-ray generator array 103 (e.g., addressability and moderate pitch spacing) also enables faster acquisition speeds as compared to conventional tomographic systems, because unlike conventional systems which typically require mechanical movement to achieve sufficient scanning angles, embodiments of the present disclosure are capable of movement-free tomosynthesis. The elimination of the need for a gantry reduces the size, weight, complexity and cost of portable x-ray source 100 as compared to conventional system. Moreover, this faster acquisition speed may reduce the amount of time patients need to stay immobile, and thus may increase patient comfort.

In one aspect of the present disclosure, portable x-ray source 100 may weigh approximately 4 kg and fit into a standard camera bag. In contrast, a standard, wall-mounted dental x-ray unit may weigh nearly 40 kg, while a two-dimensional portable system typically weights around 6 kg.

The cost of portable x-ray source 100 is also reduced by the elimination of vacuum tubes, which tend to be fragile, have a short life, and only limited use outside hospital settings. In sharp contrast, distributed x-ray generator array 103 may be made in a semiconductor foundry, which will reduce cost to manufacture, deploy, and maintain portable x-ray source 100.

The cost savings, low-profile, and portability of embodiments of the present disclosure may lessen the burden on end users, such as hospitals, primary care facilities, and dental offices, who are often required to make large capital investments in imaging systems, and thus may increase the availability of three-dimensional x-ray imaging. For example, deploying a portable three-dimensional x-ray imaging source within a multi-dentist practice would be transformative given that due to equipment cost many dentists do not have access to CBCT or other three-dimensional imaging systems, and thus are often forced to rely on limited two-dimensional planar x-ray images.

The shorter stand-off distances achievable by embodiments of the present disclosure also enable a reduction of radiation scatter (side scatter and backscatter), which in turn reduces the risk of x-ray exposure for x-ray operators and clinical workers. Scatter radiation may be further reduced by use of a gross collimator 115, which may absorb x-rays that are not useful for imaging purposes, such as x-rays outside the region of interest of object (ROI) 203, while allowing x-rays useful to imaging to strike the ROI.

Gross collimator 115 may comprise a structure made of x-ray attenuating materials (e.g., high-density material(s) with high x-ray absorption). In one aspect, gross collimator 115 may comprise an elevated plane (or walls) that limits the area illuminated by portable x-ray source 100 to a ROI. In this way, gross collimator 115 may reduce non-imaging dosages of x-ray photons by lessening, if not removing, x-ray backscatter and side-scatter. Thus, gross collimator 115 may serve to minimize unnecessary, and potentially harmful radiation exposure, without impacting x-ray image quality.

The use of such a gross collimator 115 is particularly useful for imaging where the activate area of the detectors is small, and in cases where sensitive organs are adjacent to the area to be imaged. An example of such a use case is dental imaging: the intra-oral detectors are often 2 cm×4 cm or smaller and the teeth and jaws of interest lie in close proximity to the brain.

Referring back to FIG. 1, distributed x-ray generator array 103 may comprise a plurality of electron field emitters 104 aligned or otherwise paired with a plurality of targets 106. In this way, each generator 102 may be comprised of an electron field emitter 104 paired with a target 106. Each electron field emitter 104 may be capable of generating a beam of electrons that may be directed at a target 106, such as a material effective at high-energy bremsstrahlung, to produce x-rays.

The plurality of electron field emitters 104 (and thus the plurality of targets 106) may be arranged as an emitter array 105. Emitter array 105 may comprise any of several configurations, including a two-dimensional array forming a square grid; a triangular grid also known as a "hexagon pack," or electron field emitters 104 may be randomly spaced. The spacing and pattern of emitter array 104 may be varied based on, or determined by, several factors, including the end-use, the imaging application geometry, or the desired image resolution, among others.

Electron field emitters 104 may be fabricated from a variety of conducting materials including, among others, doped silicon, tungsten or tungsten alloys, or highly conductive metals, such as copper or aluminium. Alternatively (or in conjunction), it may be desirable to overcoat electron field emitters 104 (or their tips) with a protective coating or film of tungsten, titanium-nitride, diamond-like carbon or other robust conductive material.

As noted, distributed x-ray generator array 103 may comprise a plurality of targets 106 made of one or more materials capable of converting incident electrons through physical process(es) into x-rays. In one aspect of the present disclosure, each target 106 may comprise a metal film made of a material(s) effective at high-energy bremsstrahlung, such as tungsten, molybdenum, rhenium, gold or other heavy metals. In another aspect, each target 106 may be made of two or more metals, or may comprise more than one layer of materials, such that each target 106 may include a small area comprised of an effective bremsstrahlung material (e.g., tungsten) and an adjacent area made of a low-Z material (e.g., silicon).

Targets 106 may be self-supporting, or may be supported by an electrically conducting substrate, which may serve to complete the electrical circuit (between the plurality of electron field emitters 104 and targets 106) and to dissipate the heat energy deposited by the electron beam. In one example, target 106 may comprise a thin film of tungsten supported by a silicon substrate, or another conductive, light-element material, such as aluminium. In yet another embodiment, the substrate may be made of an insulating material having a conductive coating.

Target 106 may have a variety of geometries, including, among others, a 'doughnut' shape, a circular shape, or may incorporate straight lines. As would be understood by a person of skill in the art, the thickness of target 106 may be varied depending on the atomic number of the target 106 material, the thermal properties of the target 106 material, or the energy of the electron beam that will be incident on target 106. In an aspect of the present disclosure, the thickness of each target 106 may be between 1 and 100 µm.

The electron field generated by electron field emitters 104 may be sufficiently intense to ionize gas molecules proximate to electron field emitters 104 (e.g., in the +z and/or −z planes). This ionization may prevent the production of useful x-rays because, among other things, the ionized gases may scatter the emitted electrons, and may damage electron field emitters 104 and targets 106. Accordingly, it may be desirable to minimize, if not eliminate, gas molecule ionization by maintaining a vacuum between electron field emitters 104 and targets 106 by, among other things, housing emitters 104 and targets 106 in a vacuum or low-pressure environment.

In an aspect of the present disclosure, such a vacuum (low-pressure) environment may be achieved by manufacturing distributed x-ray generator array 103 under high-vacuum, and then housing distributed x-ray generator array 103 (and thus electron field emitters 104 and targets 106) within a chamber capable of maintaining the vacuum (low-pressure) environment. The vacuum environment may be maintained through the operating life of portable x-ray source 100 by utilizing a vacuum getter, which may be capable of chemically combining or absorbing gas molecules. The vacuum getter may be coated on an internal surface or attached to the vacuum chamber that houses distributed x-ray generator array 103. As would be recognized by a person of skill in the art in view of the present disclosure, other mechanisms may be suitable for maintaining a requisite vacuum environment, such as mechanical and ion pumps.

Targets 106 may be deposited on the inner surface of the vacuum chamber, which houses distributed x-ray generator array 103. This configuration provides a vast improvement over conventional tube-based sources in that by depositing targets 106 on the inner surface of the vacuum chamber the heat generated on targets 106 may be more easily dissipated by conduction (e.g., excess heat may be dissipated throughout the chamber), making portable x-ray source 100 easier to cool than conventional systems. In stark contrast, targets or anodes in conventional x-ray sources are housed within the source vacuum tube, which makes cooling difficult because it must rely on radiation to dissipate heat.

Distributed x-ray generator array 103 may also include a gate, which may be capable of controlling the emission of electrons from electron field emitters 104. The gate may comprise a plurality of conducting structures through which electrons can pass and a voltage can be applied. Alternatively, the gate may be capable of suppressing the electron field generated between electron field emitters 104 and targets 106. By way of example, the gate may comprise a conducting plate with holes capable of allowing electrons from electron field emitters 104 to pass. In another embodiment, the gate may comprise an array of individual annular structures, each of which is associated with an electron field emitter 104. The gate may also include an insulating substrate coated with a conducting material.

In an aspect of the present disclosure, the gate may be powered by high-voltage power supply 109 of portable x-ray source 100. In another aspect, voltage to each portion of the gate associated with a particular electron field emitter 104, such as a particular set of holes or annular structures, may be controlled individually.

The gate may be altogether eliminated such that distributed x-ray generator array 103 may comprise a diode configuration (e.g., cathode and anode structures absent a gate). This diode configuration typically has a limited operating-voltage range because of the exponential nature of field emission (e.g., the emitted current depends exponentially on the applied voltage), but is simpler to produce and can be more reliable than a triode configuration, or a configuration which includes a gate.

Nonetheless, triodes may offer various benefits, including the ability to independently control the emission voltage and accelerating (or final) voltage. Accordingly, based on use and other design considerations, it may be desirable to select one configuration over another. By way of example, in the case of a dental imaging source, where fixed or nearly fixed voltages are acceptable, a diode configuration may be preferable.

Referring to FIG. 1, portable, x-ray source 100 may also include spacer 108 disposed between electron field emitters 104 and targets 106. Spacer 108 may serve to maintain the requisite separation between electron field emitters 104 and targets 106, and to insulate electron field emitters 104 from targets 106.

Spacer 108 may be varied in thickness depending on materials used and voltages applied (the potential difference between electron field emitters 104 and targets 106). For example, larger voltages may require more distance between electron field emitters 104 and targets 106, and thus may require a thicker spacer 108. Conversely, a thinner spacer 108 may be used with smaller voltages. In aspects of the present disclosure, spacer 108 may be between 1 mm to 30 mm thick. In another aspect, spacer 108 may be between 5 mm and 15 mm thick. And in yet another aspect, spacer 108 may be between 15 mm and 30 mm thick.

Spacer 108 may be made of glass, borosilicate glass, ceramic, or other suitable material as would be understood by a person of skill in the art in view of the present disclosure, and may have various configurations. In one aspect of the present disclosure, spacer 108 may be substantially cylindrical. In yet another aspect involving a triode configuration, spacer 108 may be formed of two parts, such as to allow for the separation or removal of the gate from distributed x-ray generator array 103.

Spacer 108 may further serve as part of the vacuum chamber that may house electron field emitters 104 and targets 106. Alternatively, spacer 108 may not serve to form or maintain such a vacuum.

Portable x-ray source 100 may further include a high-voltage power supply 109, which may be capable of producing a large potential difference (voltage) between electron field emitters 104 and targets 106. In an aspect of the present disclosure, high-voltage power supply 109 may be capable of converting line voltage, such as the common voltage found in a standard outlet, to high voltage. Alternatively, power supply 109 may be connected to one or more batteries 107, and may be capable of converting battery voltage to high voltage.

High-voltage power supply 109 may be capable of producing (but is not be limited to) voltages up to −120 kV. In another aspect of present disclosure, high-voltage power supply 109 may produce voltages between −20 and −120 kV. Alternatively, high-voltage power supply 109 may produce positive voltages, and in a further aspect, may operate at a fixed voltage between 50 kV-70 kV. In yet another aspect of the present disclosure, power supply 109 may be capable of operating at two or more voltages, sequentially or in parallel.

High-voltage, power supplies (e.g., −30 kV to −80 kV), as described in the present disclosure, run contrary to conventional x-ray imaging approaches. In particular, conventional approaches teach that electron field emitters are to be driven by low- to moderate—power supplies, and teach away from use of high-voltage power supplies 109. Conventional approaches also teach away from compact power supplies, where the gap between the ground and high-tension plane is minimized.

As illustrated in FIG. 1, the geometry of high-voltage power supply 109 may generally follow that of electron field emitters 104 and targets 106, and the output plane of high-voltage power supply 109 may touch electron field emitters 104 to form an electrical contact. In an aspect of the present disclosure suitable for dental radiology, high-voltage power supply 109 may be 30 mm thick with a transverse size of 150 mm by 150 mm. Portable, x-ray source 100 may be packaged in liquid (insulating oils) and/or solid (putty, potting), so as to provide the insulation required for the high-voltage of high-voltage power supply 109.

In another embodiment (not illustrated), distributed x-ray generator array 103 may be powered by a plurality of ferroelectric crystals as described in PCT/US2010/044762. Alternatively, as would be understood by a person of skill in view of the present disclosure, distributed x-ray generator array 103 may be powered by any number of devices capable of producing the desired voltage.

Portable x-ray source 100 may further include a plurality of emission controls 110. The plurality of emission controls 110 may be capable of controlling (e.g., defocusing/focusing or deflecting/steering) electrons emitted by electron field emitters 104. In this way, emission control 110 may be capable of regulating the emission of x-rays by each generator 102. In turn, this enables each generator 102 to be individually addressable (controllable) and thus enables distributed x-ray generator array 103 to generate temporally-separated, but physically overlapping x-ray conelets. This allows for seamless coverage of an object to be imaged, and maximal use of the available flux while maintaining the ability to have minimal stand-off distances.

The plurality of emission controls 110 may be capable of defocusing/focusing or deflecting/steering electron beams from an electron field emitter 104, individually onto or away from target 106, and thus may affect the production or cessation of x-rays respectively. It will be appreciated by one skilled in the art that emission control is not limited to one approach, and may be used in combination with one or more methods, including through electro-static, magneto-static and electro-magnetic means. One such approach is described in PCT/GB2015/050639.

Figure 3:
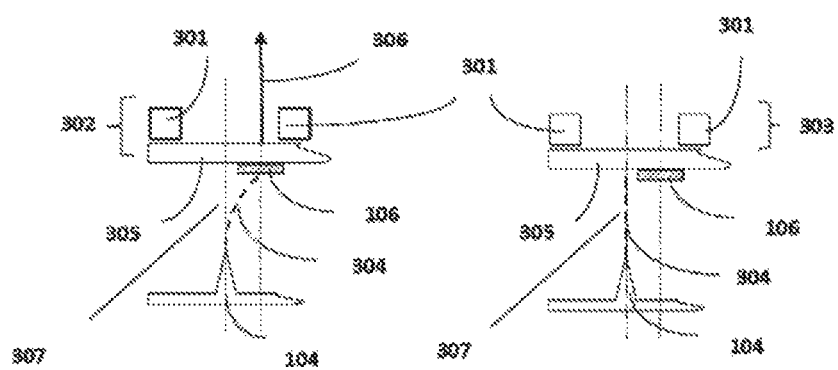
FIG. 3 shows an example of a plurality of emission controls in accordance with aspects of the present disclosure.

FIG. 3 shows an example of a plurality of emission controls 110 comprising a plurality of selectively-powered coils or magnets (coils/magnets) 301. Coils/magnets 301 may be capable of preventing electron beams 304 emitted by an electron field emitter 104 from striking a portion of a target 106 comprised of a material effective at high-energy bremsstrahlung, and thus may be capable of controlling x-ray emission.

As illustrated in FIG. 3, the output flux (electron beam 304) of electron field emitter 104 may be controlled by using electromagnetic fields generated by coils/magnets 301 such that when energized or "on" 302 the fields produced deflect the electron beam 304 away from the ballistic trajectory/axis 307 and onto target 106. When coils/magnets 301 are "off" 303, the electron beam 304 continues directly on axis 307 and strikes substrate 305, which may be comprised of low atomic number materials which only generates low energy photons that produce no signal. Thus, the state of coils/magnets 301 (on 302 or off 303) serves as a control of the generation of x-rays 306 from a given emitter.

In an aspect of the present disclosure, target 106 may comprise a discrete area made of an effective bremsstrahlung material, such as tungsten, an adjacent area made of a low-Z material, such as silicon, and a support made of a conductive material, such as aluminum. Lenses or yokes maybe used to elongate the magnetic field in the beam axis direction, and compact it off axis.

In a further embodiment of the present disclosure, the individual selectively-powered coils/magnets 301 may be arranged in clusters of coils/magnets in a pattern essentially equivalent to that of emitter array 105. The clusters may comprise four coils/magnets 301 capable of creating a dipole magnetic field arranged about each electron field emitter 104. Alternatively, the clusters may comprise eight or more coils/magnets 301 arranged such that a central set of coils creates a dipole field for deflecting the beam trajectory of the electron field emitter 104 and surrounding coils/magnets 301 are used to offset the stray field of the central coils/magnets 301, these clusters being configured in a pattern essentially equivalent to that of emitter array 105.

In aspects of the present disclosure, it may be necessary for solenoid coil 301 to deflect the electron beam a distance of 0.1 mm to 1.25 mm from the nominal path. PCT/GB2015/050639 describes methods of achieving such deflection using high-current coils. Notably, using clusters of coils, as described herein, similar results may be achieved at low currents.

Portable x-ray source 100 may also include a mechanism capable of selectively controlling x-ray emission from distributed x-ray generator array 103. In an aspect of the present disclosure, said mechanism may comprise a circuit(s), such as an addressing and timing circuit(s), capable of selectively activating one or more controller 110, such as solenoid coils 301, in a predetermined sequence. Targets 106 and the plurality of emission controllers 110 may be arranged such that portable x-ray source 100 operates normally in the on mode. Alternatively, they may be arranged such that portable x-ray source 100 operates in normally off mode. In addition, the control mechanism (e.g., electronic circuit) may be capable of automatically stopping the emission of x-ray photons after a predetermined detector signal level is achieved.

Portable x-ray source 100 may also include a filter capable of removing or blocking radiation that does not contribute to x-ray imaging, such as low-energy x-rays entirely absorbed by tissue. In this way, the filter may be able to minimize unnecessary x-ray exposure to patients, radiographers, technologists, clinicians, dentists, etc., without negatively impacting x-ray imaging. In an aspect of the present disclosure, the filter may be removable. The filter may also be encoded such that control electronics can determine the specific filter in use.

As would be understood by a person of skill in view of the present disclosure, the filter may be made of a variety of materials and may have varying thickness depending on the operating voltage or desired end use of portable x-ray source 100. As an example, the filter may comprise an aluminium sheet between 1 mm to 10 mm thick. Alternatively, the filter may comprise a copper sheet between 1 mm to 5 mm thick. In yet another aspect, the filter may comprise a stack of alternating higher-atomic number and lower-atomic number materials, such as aluminum and carbon.

Portable x-ray source 100 may include a collimator array, which may serve to narrow the angle of emitted x-rays, and thus further facilitates fractional coverage of a region of interest. The collimator array may be as described in PCT/GB2015/050637 to Travish, et al. Alternatively, the collimator array may comprise a plate made of high-density material having a plurality of holes of appropriate size, wherein the holes are capable of allowing x-rays to be transmitted with a specific opening angles. Such high-density material may include tungsten, steel, or an alloy made of similar materials having a high x-ray attenuation coefficients.

In another aspect of the present disclosure, the collimator array may comprise a plurality of tubes, wherein each tube may be capable of controlling the opening angle of emitted x-ray cones. For example, the collimator array may comprise a tungsten plate having a plurality of aluminium inserts, wherein each aluminium insert serves to transmit a portion of each x-ray cone with a well-defined opening angle. In another embodiment, the collimator array may comprise two plates arranged one atop of the other with each plate having a plurality of holes such that a particular x-ray cone passes through a hole in the lower and then in the upper plate.

Portable x-ray source 100 may include a housing 101. Housing 101 may comprise a light, protective casework capable of providing a mechanically rigid platform for x-ray source 100 and facilitating portability. Housing 101 may also be capable of aiding in thermal control, for example by dissipating heat throughout housing 101. In a preferred aspect of the present disclosure, housing 101 is compatible with medical device requirements such as sterility, alcohol, wipe down, and cytotoxicity.

Housing 101 may also include a mechanism for aligning portable x-ray source 100 to a detector, such as one or more non-contact sensors capable of providing the user of portable x-ray source 100 with an indication that portable x-ray source 100 is in proper alignment with a detector. In another aspect of the disclosure, housing 101 may comprise an inner case designed to enclose high-voltage components, such as distributed x-ray generator array 103, and an outer case designed to hold other, non-high voltage components. The inner case of housing 101 may be filled with insulating fluid, or alternatively with a solid insulator. Housing 101 may also house batteries 107 to power portable x-ray system 101 without need for wall plug supplied electricity.

The invention claimed is:

1. A portable x-ray source, comprising:
a distributed x-ray generator array;
a circuit capable of selectively controlling the emission of x-rays by the distributed x-ray generator array;
a power supply capable of producing high voltages for powering the distributed x-ray generator array; and
a gross collimator, wherein the distributed x-ray generator array comprises:
a plurality of electron field emitters;
a plurality of targets, wherein each target is capable of emitting x-ray photons when electrons are incident upon an area of said target comprised of a material effective at high-energy bremsstrahlung, and wherein the plurality of targets each are positioned entirely separate from a straight axis from any electron field emitter along which electrons emitted by the electron field emitters travel;
a spacer disposed between the electron field emitters and targets, wherein said spacer is capable of withstanding a high potential difference between the electron field emitters and targets;
a plurality of emission controls capable of preventing electrons emitted by the electron field emitters from striking the area of said targets comprised of a material effective at high-energy bremsstrahlung;
a low pressure enclosure containing said electron field emitters and targets; and
a filter capable of filtering low-energy x-rays.

2. The portable x-ray source of claim 1, wherein the distributed x-ray generator array further comprises a plurality of gates, wherein each gate is capable of controlling the emission field of an associated electron field emitter.

3. The portable x-ray source of claim 1, wherein the distributed x-ray generator array further comprises a collimator array comprised of a plurality of collimators, wherein each collimator is capable of narrowing the angle of x-rays emitted by an associated target.

4. The portable x-ray source of claim 1, wherein the distributed x-ray generator array further comprises a fixed array.

5. The portable x-ray source of claim 1, wherein the distributed x-ray generator array further comprises a planar array.

6. The portable x-ray source of claim 1, wherein the plurality of emission controls comprises one of a plurality of electromagnetic coils or a plurality of parallel-plate deflectors configured to selectively activate and when activated generate an electric or magnetic field that deflects the electrons from the axis and onto the targets.

7. The portable x-ray source of claim 1, further comprising a housing; wherein said housing comprises an inner enclosure which isolates high-voltage components of the x-ray source, and an outer enclosure which contains other components of the x-ray source.

8. The portable x-ray source of claim 1, further comprising one or more sensors, wherein said one or more sensors enable the distributed x-ray generator array to be aligned to a detector without requiring contact between the distributed x-ray generator array and the detector.

9. The portable x-ray source of claim 1, wherein the power supply is capable of converting battery voltage to said high voltages for powering the distributed x-ray generator array without reliance on external power.

10. The portable x-ray source of claim 1, wherein the power supply is capable of converting line voltage to said high voltages for powering the distributed x-ray generator array.

11. The portable x-ray source of claim 1, wherein the power supply is capable of producing voltage in the range of −30 kV to −80 kV.

12. The portable x-ray source of claim 1, wherein the power supply is capable of operating at substantially one fixed voltage.

13. The portable x-ray source of claim 1, wherein the circuit comprises a digital addressing and timing circuit.

14. The portable x-ray source of claim 1, wherein the circuit is capable of automatically stopping the emission of x-ray photons after a predetermined detector signal level is achieved.

15. The portable x-ray source of claim 1, wherein the portable x-ray source is capable of being used for dental imaging to generate a three-dimensional image set.

16. The portable x-ray source of claim 1, wherein the distributed x-ray generator array has a moderate pitch spacing in the millimeter to centimeter range.

17. The portable x-ray source of claim 1, wherein the x-ray source weighs less than 5 kg.

18. A portable x-ray source, comprising:
a distributed x-ray generator array;
a means of producing high voltages, wherein said high voltages are capable of powering the distributed x-ray generator array; and
a means for collimating x-rays emitted by the distributed x-ray generator array to be within an area at a given distance, wherein the distributed x-ray generator array comprises:
a plurality of electron field emitters;
a plurality of targets, wherein each target is capable of emitting x-ray photons when electrons are incident upon said target, wherein each target is aligned with an electron field emitter;
a means of selectively controlling the emission of x-rays from the distributed x-ray generator array, wherein the means of selectively controlling the emission is located behind the targets in a direction away from the electron field emitters;
a means of withstanding high-voltage between the electron field emitters and the targets;
a means of spacing the electron field emitters from the targets;
an enclosure wherein said plurality of electron field emitters and plurality of targets are maintained in a vacuum; and
a means of filtering low-energy x-ray photons.

19. The portable x-ray source of claim 18, wherein the distributed x-ray generator array further comprises a plurality of gates;
a means of spacing the gates from the electron field emitters;
a means of powering the gates; and
a means of spacing the gates from the targets.

20. A portable x-ray source, comprising:
a distributed x-ray generator array, wherein the distributed x-ray generator array includes,
a plurality of electron field emitters;
a plurality of targets each positioned entirely separate from a straight axis from any electron field emitter along which electrons emitted by the electron field emitters travel, wherein the plurality of targets are fabricated of materials that emit x-ray photons via high-energy bremsstrahlung radiation when impacted by the electrons,
a spacer disposed between the electron field emitters and targets, and
a plurality of emission controls positioned around the axis, wherein the plurality of emission controls are configured to selectively activate and when activated generate an electric or magnetic field that deflects the electrons from the axis and onto the targets; and
a power supply for powering the distributed x-ray generator array.

* * * * *